US010702665B2

(12) United States Patent
Gardner

(10) Patent No.: US 10,702,665 B2
(45) Date of Patent: Jul. 7, 2020

(54) BI-FUNCTIONAL INTUBATING AND VENTILATING SUPRAGLOTTIC AIRWAY

(71) Applicant: Glenn P. Gardner, Oak Brook, IL (US)

(72) Inventor: Glenn P. Gardner, Oak Brook, IL (US)

( * ) Notice: Subject to any disclaimer, the term of this patent is extended or adjusted under 35 U.S.C. 154(b) by 0 days.

(21) Appl. No.: 16/687,877

(22) Filed: Nov. 19, 2019

(65) Prior Publication Data

US 2020/0155781 A1 May 21, 2020

Related U.S. Application Data

(60) Provisional application No. 62/916,386, filed on Oct. 17, 2019, provisional application No. 62/916,398, filed on Oct. 17, 2019, provisional application No. 62/769,725, filed on Nov. 20, 2018.

(51) Int. Cl.
    *A61M 16/04* (2006.01)
(52) U.S. Cl.
    CPC .... *A61M 16/0488* (2013.01); *A61M 16/0402* (2014.02); *A61M 16/0434* (2013.01); *A61M 16/0486* (2014.02)
(58) Field of Classification Search
    CPC .......... A61M 16/0488; A61M 16/0434; A61M 16/0486; A61M 25/0668; A61M 25/0169; A61M 39/08; A61M 39/105; A61M 2039/082
    See application file for complete search history.

(56) References Cited

U.S. PATENT DOCUMENTS

| 5,477,851 | A | 12/1995 | Callaghan et al. |
| 5,623,921 | A | 4/1997 | Kinsinger et al. |
| 6,070,581 | A | 6/2000 | Augustine et al. |
| 2002/0170556 | A1* | 11/2002 | Gaitini .................. A61M 16/04 128/200.14 |

(Continued)

FOREIGN PATENT DOCUMENTS

| CN | 209137662 U | 7/2019 |
| EP | 1528944 B1 | 7/2009 |

(Continued)

OTHER PUBLICATIONS

PCT International Search Report and Written Opinion, Application No. PCT/US19/62109, dated Feb. 3, 2020.

*Primary Examiner* — Timothy A Stanis
*Assistant Examiner* — Cana A Gallegos
(74) *Attorney, Agent, or Firm* — MacMillan, Sobanski & Todd, LLC

(57) ABSTRACT

A bi-functional intubating and ventilating supraglottic airway includes a supraglottic bowl defining a distal end, a neck extending outward of the supraglottic bowl and defining a proximal end, and a longitudinally extending intubation conduit formed therethrough. The supraglottic bowl includes a cuff and defines a bowl surface, wherein the intubation conduit extends from the proximal end of the neck to an opening in the bowl surface, and wherein the intubation conduit is configured to have an endotracheal tube inserted therethrough. At least one fluid flow channel is (Continued)

formed longitudinally through a wall of the supraglottic airway, collaterally to the intubation conduit, from the proximal end to the bowl surface within the supraglottic bowl.

31 Claims, 12 Drawing Sheets

(56) References Cited

U.S. PATENT DOCUMENTS

| | | |
|---|---|---|
| 2005/0081861 A1 | 4/2005 | Nasir |
| 2005/0139220 A1 | 6/2005 | Christopher |
| 2014/0276178 A1 | 9/2014 | Simon |
| 2016/0184542 A1 | 6/2016 | Esnouf |
| 2016/0256651 A1 | 9/2016 | Molnar |
| 2016/0331918 A1 | 11/2016 | Nasir et al. |
| 2017/0232216 A1 | 8/2017 | Nave et al. |
| 2018/0104427 A1 | 4/2018 | Avitsian et al. |
| 2018/0169365 A1 | 6/2018 | Sawyer et al. |
| 2018/0242833 A1 | 8/2018 | Gardner |
| 2020/0001032 A1 * | 1/2020 | Zhou ................ A61M 16/0418 |

FOREIGN PATENT DOCUMENTS

| | | |
|---|---|---|
| GB | 2472063 B | 6/2011 |
| WO | 2015152985 A1 | 10/2015 |
| WO | 2018060062 A1 | 4/2018 |

* cited by examiner

BI-FUNCTIONAL INTUBATING AND VENTILATING SUPRAGLOTTIC AIRWAY

This invention relates in general to a device to safely and simultaneously ventilate and intubate a patient. In particular, this invention relates to an improved bi-functional intubating and ventilating supraglottic airway configured to ventilate and have an endotracheal tube (ETT) carried therein.

Conventional supraglottic airways (SGA) and laryngeal mask airways (LMA) are orally inserted airway devices placed in the larynx of a patient to provide a clear, open, and unobstructed conduit or channel to deliver oxygen, air, or other gases to the lungs via the trachea. Conventional SGAs and LMAs have a conventional 15 mm connector at their proximal ends to provide a sealed connection to a standard anesthetic circuit or bag-valve-mask system. At the distal ends of the SGAs and LMAs there is a bowl designed to create a seal within the airway, or to direct the flow of gases to the trachea instead of the esophagus. Thus, a conduit or channel that connects the 15 mm connector to the bowl allows for unobstructed passage of oxygen, air, or other gases to the trachea.

This conduit or channel with the bowl feature also provides a passageway for endotracheal intubation. This feature of conventional SGAs may also be enhanced by being combined with a flexible video-scope or a fiber-optic scope. Unfortunately, after endotracheal intubation is performed using an SGA or LMA, the endotracheal tube (ETT) must be disassembled, secured, and reassembled so that the SGA may be removed.

This process also requires an interruption of ventilation while the ETT 15 mm connector of the ETT is removed and stored, an ETT retrieval stick is placed on the ETT shaft, the SGA is removed while supporting the ETT in position, the retrieval stick is removed, and lastly, the 15 mm connector is replaced before a user can ventilate the patient. Alternatively, the SGA or LMA and the ETT may be left in place and together, but with such an arrangement, the ability to directly secure the ETT in place in the patient is then inhibited.

One known type of SGA is configured such that a tube portion of the SGA may be split longitudinally. One example of such a split SGA is described in U.S. Pat. No. 5,623,921 to Kinsinger, in EP Patent No. 1528944 B1 to Muhammed Nasir, in UK Patent Application No. GB 2472063 to Vikas Sharma, and in Chinese Patent Application No. CN 209137662U to Fang Yafei. These split SGA devices allow endotracheal intubation via longitudinal airway channels therein and eliminate the need to disassemble the ETT in order to remove the SGA device. Unfortunately, a user you must still use the same airway channel for the ventilation and for the intubation and thus must stop ventilation to perform the intubation. U.S. Patent Publication No. 2014/0276178 A1 to Simon discloses a multi-lumen breathing tube device that has two channels, both of which are designed for ventilation. It would therefore be desirable to provide a device to safely and simultaneously ventilate and intubate a patient.

SUMMARY OF THE INVENTION

This invention relates to an improved supraglottic airway configured to ventilate and have an endotracheal tube (ETT) carried therein such that a patient may be simultaneously ventilated and intubated.

In a first embodiment, a bi-functional intubating and ventilating supraglottic airway is configured to ventilate and have an ETT carried therein and includes a supraglottic bowl defining a distal end, a neck extending outward of the supraglottic bowl and defining a proximal end, and a longitudinally extending intubation conduit formed therethrough. The supraglottic bowl includes a cuff and defines a bowl surface, wherein the intubation conduit extends from the proximal end of the neck to an opening in the bowl surface, and wherein the intubation conduit is configured to have an endotracheal tube inserted therethrough. At least one fluid flow channel is formed longitudinally through a wall of the supraglottic airway, collaterally to the intubation conduit, from the proximal end to the bowl surface within the supraglottic bowl.

In a second embodiment, the bi-functional intubating and ventilating supraglottic airway includes a supraglottic bowl defining a distal end, a neck extending outward of the supraglottic bowl and defining a proximal end, and a longitudinally extending intubation conduit formed therethrough. The supraglottic bowl includes a cuff and defining a bowl surface, wherein the intubation conduit extends from the proximal end of the neck to an opening in the bowl surface, and wherein the intubation conduit is configured to have an endotracheal tube (ETT) inserted therethrough. A plurality of fluid flow channels is formed longitudinally through a wall of the supraglottic airway from the proximal end to the bowl surface within the supraglottic bowl. One or more of the fluid flow channels are configured as ventilation channels that allow for patient ventilation simultaneously with, and independent of patient intubation. The supraglottic airway further includes an intubation conduit occluding feature, and a sealable slot having an elongated, air-tight closure. A tube assembly extends outwardly from the proximal end of the supraglottic airway, the tube assembly including a plurality of first fluid flow tubes, the distal ends of which are connected within the fluid flow channels, the proximal ends of which merge into a single second fluid flow tube and a 15 mm connector at the proximal end of the second fluid flow tube. A connector is configured to releasably connect the second fluid flow tube to the ETT.

In a third embodiment, the bi-functional intubating and ventilating supraglottic airway includes a supraglottic bowl defining a distal end, a neck extending outward of the supraglottic bowl and defining a proximal end, and a longitudinally extending intubation conduit formed therethrough. The supraglottic bowl includes a cuff and defines a bowl surface, wherein the intubation conduit extends from the proximal end of the neck to an opening in the bowl surface, and wherein the intubation conduit is configured to have an endotracheal tube (ETT) inserted therethrough. A plurality of ventilation channels is formed longitudinally through a wall of the supraglottic airway from the proximal end to the bowl surface within the supraglottic bowl. A sealable slot extending along an entire length of the intubation conduit, the sealable slot extends through the neck, the cuff, and the bowl surface, and an air-tight closure extends along the length of the sealable slot. A gastric suction channel is formed longitudinally through the wall of the supraglottic airway from the proximal end of the neck to a distal end of the cuff of the bowl. A video imaging channel is formed longitudinally through the wall of the supraglottic airway from the proximal end of the neck to the bowl surface, the video imaging channel having a video imaging device mounted therein, wherein the opening of the video imaging channel includes a normally closed one-way valve.

Various aspects of this invention will become apparent to those skilled in the art from the following detailed description of the preferred embodiments, when read in light of the accompanying drawings.

DETAILED DESCRIPTION OF THE PREFERRED EMBODIMENTS

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Figure 1:
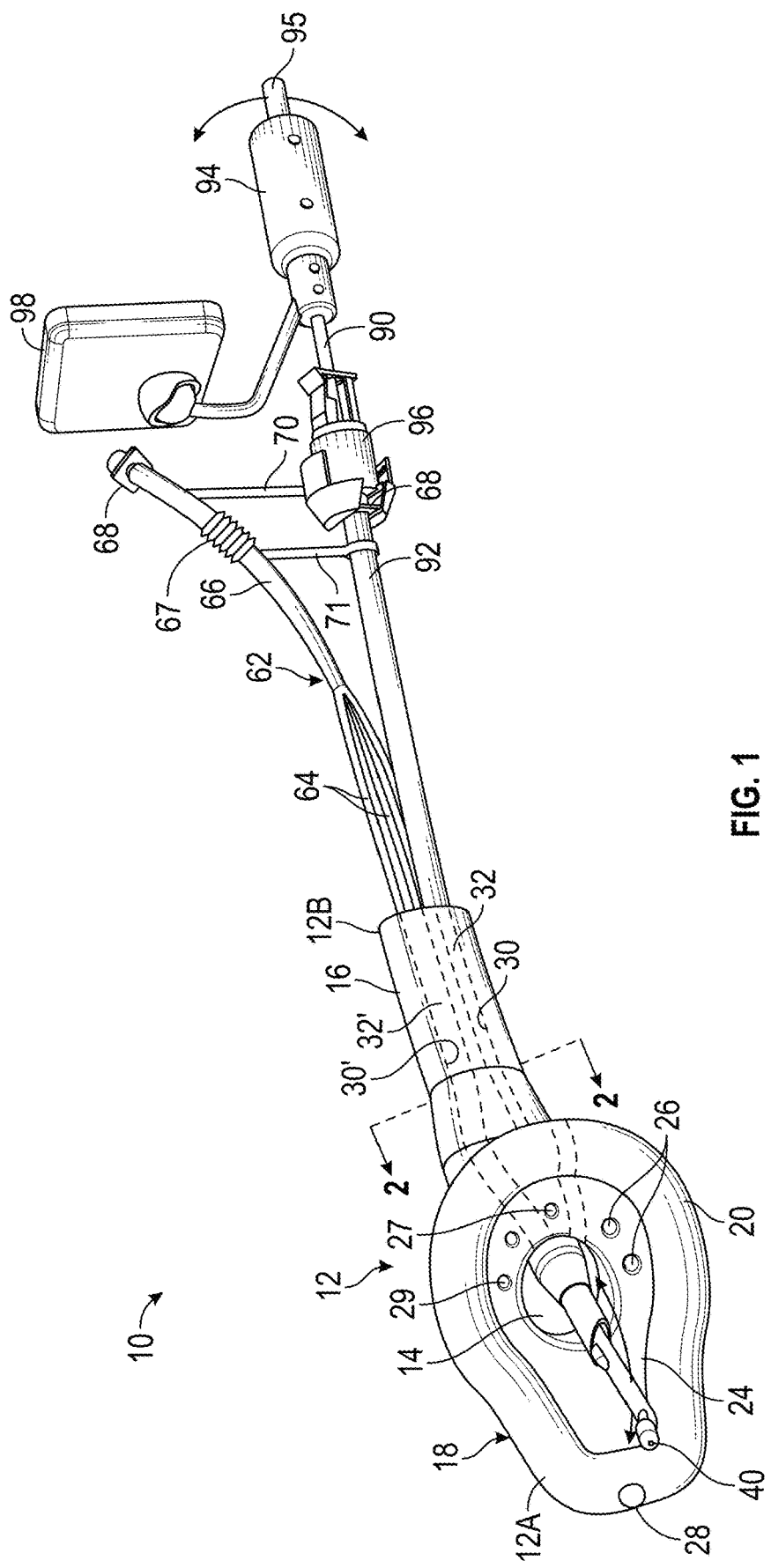
FIG. 1 is a perspective view of a first embodiment of the improved supraglottic airway assembly according to this invention.

Referring now to the drawings, a first embodiment of an improved supraglottic airway assembly is indicated at 10 in FIG. 1. The supraglottic airway assembly 10 is shown having an introducing stylet 90 with an endotracheal tube (ETT) 92 mounted thereon extending through the supraglottic airway assembly 10. The supraglottic airway assembly 10 is thus configured to ventilate and have the ETT 92 carried therein such that a patient may be simultaneously ventilated and intubated. The supraglottic airway assembly 10 includes a supraglottic airway (SGA) 12 having a first or distal end 12A, a second or proximal end 12B, and a longitudinally extending intubation conduit 14 formed therethrough. The introducing stylet 90 and the ETT 92 mounted thereon are substantially the same as the introducing stylet and the ETT 92 described in U.S. patent application Ser. No. 16/671,474 to Glenn P. Gardner filed Nov. 1, 2019.

As shown in FIG. 1, a handle 94 is attached to a proximal end of the introducing stylet 90. An attachment member 96 is configured to releasably attach the proximal end of the introducing stylet 90 to a 15 mm connector 68 of the ETT 92. The handle 94 may have a video monitor 98 attached thereto. A mechanism for controlling an articulating joint (not shown) of the introducing stylet 90 and thus for moving a distal end thereof may be controlled by any desired mechanism, such as with a control lever 95 operatively attached to the handle 94.

The SGA 12 includes an elongated body or neck 16 formed at the proximal end 12B thereof and a supraglottic bowl 18 formed at the distal end 12A thereof and extending from the neck 16. The supraglottic bowl 18 includes a cuff 20 and a bowl surface 24 within the cuff 20. The intubation conduit 14 extends from the proximal end 12B to an opening in the bowl surface 24 of the supraglottic bowl 18 at the distal end 12A. The SGA 12 may be formed having a neck 16 of any desired length. Alternatively, the SGA 12 may be formed having no neck 16.

The illustrated intubation conduit 14 has a substantially oval cross-sectional shape, however the intubation conduit 14 may have any desired cross-sectional shape, such as substantially circular, and substantially rectangular. The intubation conduit 14 may have any desired diameter or cross-sectional size. It will be understood however, that the intubation conduit 14 will preferably have a diameter or cross-sectional size that is at least slightly larger than an outside diameter of the ETT 92 that will be inserted therethrough. For example, the intubation conduit 14 may have a diameter configured for the insertion of any size ETT 92, including a pediatric ETT having an outside diameter of about 3.0 mm, a large adult ETT having an outside diameter of about 12.0 mm, or an ETT having any other outside diameter.

A plurality of fluid flow channels 26 may be formed longitudinally through the neck 16 to the bowl surface 24. In FIG. 1 five such fluid flow channels 26 are illustrated, however any desired number of fluid flow channels 26 may be formed in the SGA 12. One or more of the fluid flow channels 26 may be configured as ventilation channels. When one or more of the fluid flow channels 26 are configured as ventilation channels, the SGA 12 advantageously allows for patient ventilation simultaneously with, and independent of patient intubation.

Figure 4:
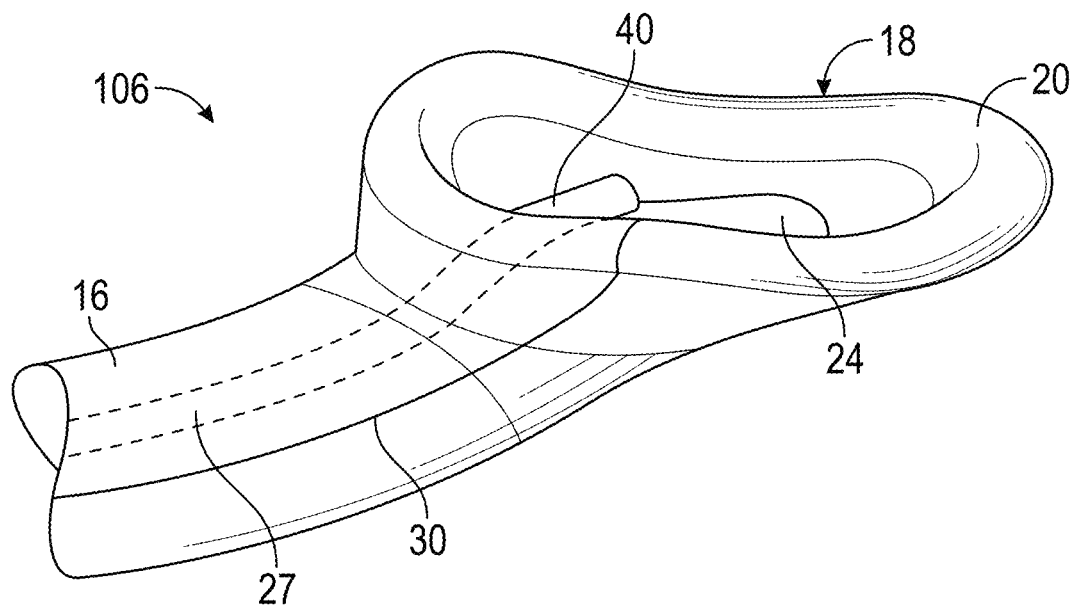
FIG. 4 is a perspective view of an alternate embodiment of the SGA illustrated in FIG. 1 showing the protruding video imaging device or channel.

Additionally, one of the fluid flow channels may be configured as a video imaging channel, such as shown at 27 in FIG. 1. The imaging channel 27 may enclose a permanently affixed video camera component or device 40, or be a passive channel for an externally acquired and inserted flexible video camera such as a disposable flexible bronchoscope. Referring to FIG. 4, a perspective view of an alternate embodiment of the SGA is shown at 106 and includes the neck 16, the supraglottic bowl 18, the cuff 20, the bowl surface 24, a sealable slot 30 (described in detail below), and the intubation conduit (not shown). The SGA 106 also includes the video imaging device 40 that may be formed or mounted in a distal end of the video imaging channel 27 such that any required connector, such as an electrical wire (not shown) may extend longitudinally through the video imaging channel 27 and outward the proximal end thereof. As shown in FIG. 1, the imaging device 40 may be formed or mounted in a distal end of the introducing stylet 90. It will be understood that the introducing stylet 90 may be formed with or without the imaging device 40.

Figure 10:
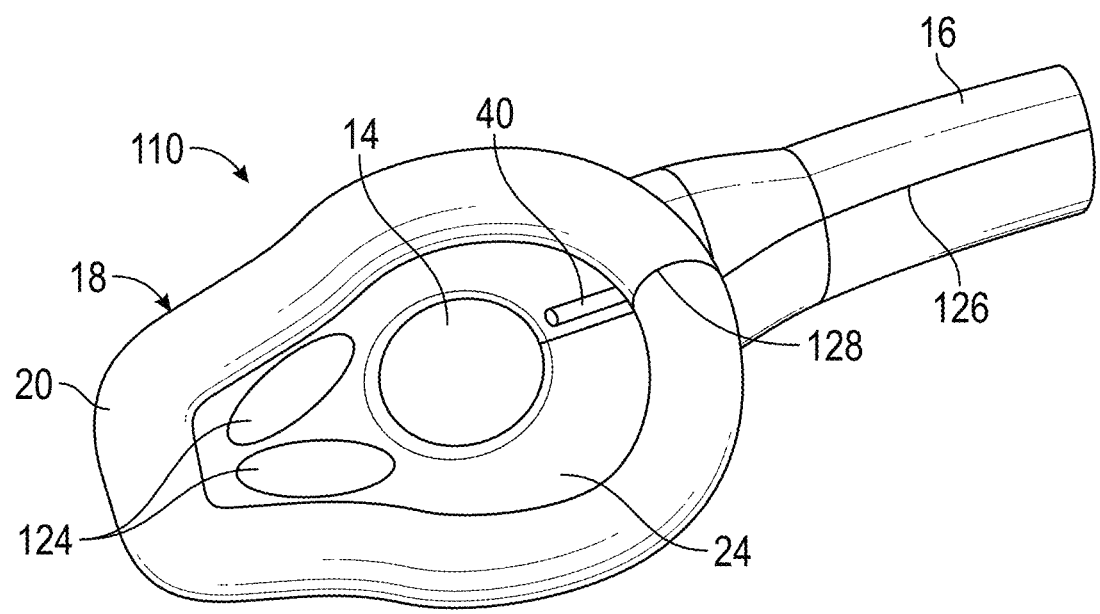
FIG. 10 is a top plan view of a portion of an alternate embodiment of the SGA illustrated in FIG. 1, showing the protruding video imaging device or channel, a fourth embodiment of the sealable slot, and a third alternate embodiment of the ventilation channels.

The video imaging device 40 may be any desired video imaging device, such as a Complementary Metal Oxide Silicon (CMOS) camera, a Charge-Coupled Device (CCD), fiber optic camera, video chip, and any other direct or indirect imaging device with a wide, normal, or narrow angle lens. The video imaging device (shown in FIGS. 4, 10, and 19) is operationally connected, for example wired or wirelessly connected, to a monitor, such as the video monitor 98. It will be understood that the video imaging device 40, or a portion of the video imaging channel 27 may extend outwardly from the bowl surface 24 into the supraglottic bowl 18, as shown in FIG. 10. This protruding video imaging device 40 may be configured to be articulated or may be formed from malleable material. As used herein, malleable is defined as any material that is able to be bent or otherwise shaped and reshaped without breaking or cracking and having shape memory, wherein the shape into which the malleable material has been bent is retained until it has been again bent or shaped.

Additionally, a gastric suction channel 28 may be formed longitudinally through the neck 16 to a distal end 12A of the cuff 20 of the supraglottic bowl 18, as best shown in FIG. 1.

If desired, one of the fluid flow channels may be configured as a glottic suction channel, such as shown at 29 in FIG. 1. If so configured, a proximal end of the glottic suction channel 29 would not extend into, or be part of, a tube assembly 62, described below. It will be understood that any desired number of fluid flow channels 26 may be formed in the SGA 12 and may terminate at any desired location in the bowl surface 24 or the cuff 20. For example, FIGS. 10, and 14 through 19, described below, illustrate alternate embodiments of the SGA 12 having alternate arrangements of the fluid flow channels 26.

A tube assembly 62 extends outwardly from the proximal end 12B of the SGA 12 and includes a plurality of first fluid flow tubes 64, the proximal ends of which merge into a single second fluid flow tube 66. A conventional 15 mm connector 68 is attached to, or formed on, a proximal end of the second fluid flow tube 66. A distal end of each of the plurality of first fluid flow tubes 64 is connected within one of the fluid flow channels 26. The conventional 15 mm connector 68 is configured for attachment to a source of oxygen or air in a known manner. The second fluid flow tube 66 may include a corrugated and expandable portion 67 configured to allow the second fluid flow tube 66 to be selectively longitudinally expanded or lengthened, and to allow the second fluid flow tube 66 to be positioned at a plurality of angles relative to the source of oxygen or air to which the second fluid flow tube 66 is connected. Alternatively, the second fluid flow tube 66 may include other types of flexible, extendable, or expandable material to allow the second fluid flow tube 66 to be selectively longitudinally expanded or lengthened, and to be positioned at a plurality of angles relative to the source of oxygen or air.

Preferably, a connector releasably connects the second fluid flow tube 66 to the attachment member 96 or to the ETT 92. In FIG. 1, alternate embodiments of the connector are shown schematically at 70 and 71. The connector 70 or 71 may be configured as a support bracket, a clamp, a rail, and the like. The connector 70 or 71 may also be rigid, fixed, telescoping, or hinged or otherwise foldable so as to allow the user to change the relative distance between the second fluid flow tube 66 and the attachment member 96 or the ETT 92.

The sealable slot 30 is formed along the entire length of the intubation conduit 14, from the proximal end 12B of the neck 16 to the opening of the intubation conduit 14 in the bowl surface 24 of the supraglottic bowl 18, and continuously through the bowl surface 24 and the cuff 20. Preferably, the sealable slot 30 includes an elongated, air-tight closure 32 along its length, such that when the air-tight closure 32 is opened, the slot 30 is defined. The slot 30 facilitates removal of the introducing stylet and ETT 92, as described in detail below. One example of an alternate location for the slot and closure is shown at 30' and 32', respectively. It will be understood however, that the SGA 12 may be formed without the sealable slot 30 and its associated elongated, air-tight closure 32.

Alternatively, the SGA 12, including the neck 16, the cuff 20, and the bowl surface 24 of the supraglottic bowl 18 may be split-capable. For example, the location desired for the slot 30 may be scored such as with cuts that penetrate only through a portion of a thickness of the wall of the SGA 12, such that the slot 30 is air-tight and un-opened until the scored slot 30 is separated with a gentile force by the user.

The slot 30 may also be closed by a re-sealable closure, such as with a two-part strip along the slot 30 that can be pressed together and readily reopened, such as a Ziploc® closure.

Figure 17:
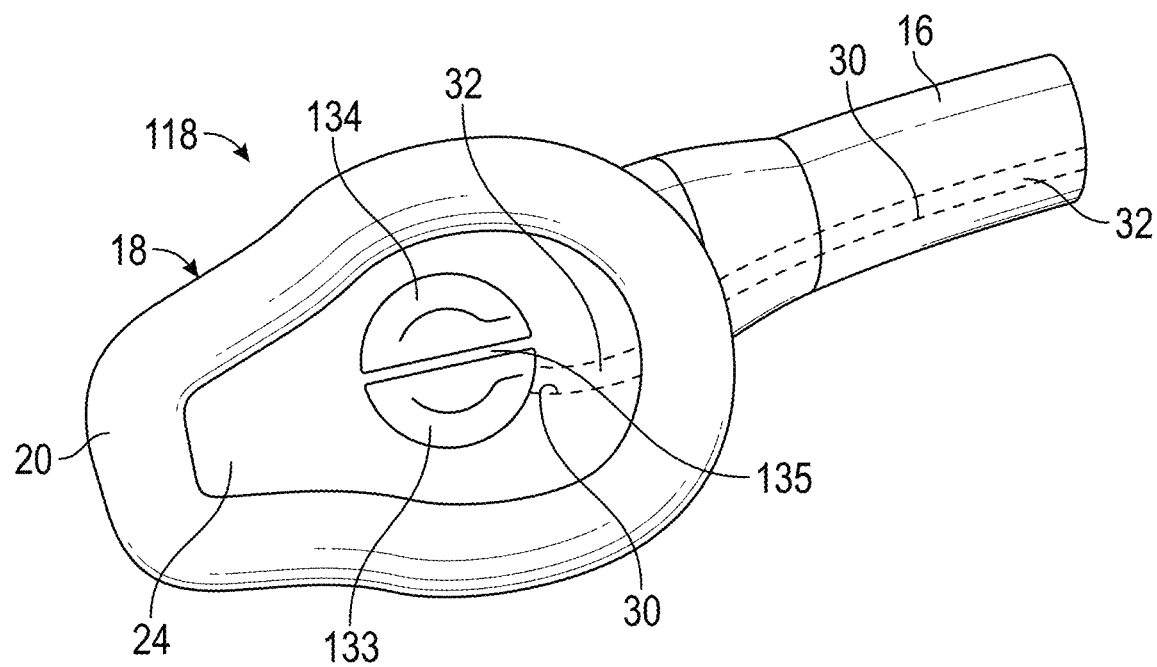
FIG. 17 is a top plan view of a portion of an alternate embodiment of the SGA illustrated in FIG. 1, showing an alternate embodiment of the intubation conduit and an eighth alternate embodiment of the ventilation channel.

If desired, the slot 30 may be formed only in the neck 16, but not in the supraglottic bowl 18. Additionally, the supraglottic cuff 20 of the supraglottic bowl 18, or a portion thereof, may be formed from an expandable or stretchable material in lieu of the slot 30 that will allow the supraglottic bowl 18 to be expanded and removed from around the ETT 92 and its 15 mm connector 68 without the need for the slot 30 in the supraglottic bowl 18. Thus, as shown in FIG. 17, the slot 30 may be formed in the neck 16 and in the bowl surface 24, but not in the supraglottic cuff 20 of the supraglottic bowl 18. Accordingly, when the supraglottic cuff 20, or a portion thereof, is formed from an expandable or stretchable material as described above, the supraglottic bowl 18 may be expanded and removed from around the ETT 92 and its 15 mm connector 68 without the need for the slot 30 in the supraglottic cuff 20 of the supraglottic bowl 18.

Figure 2:
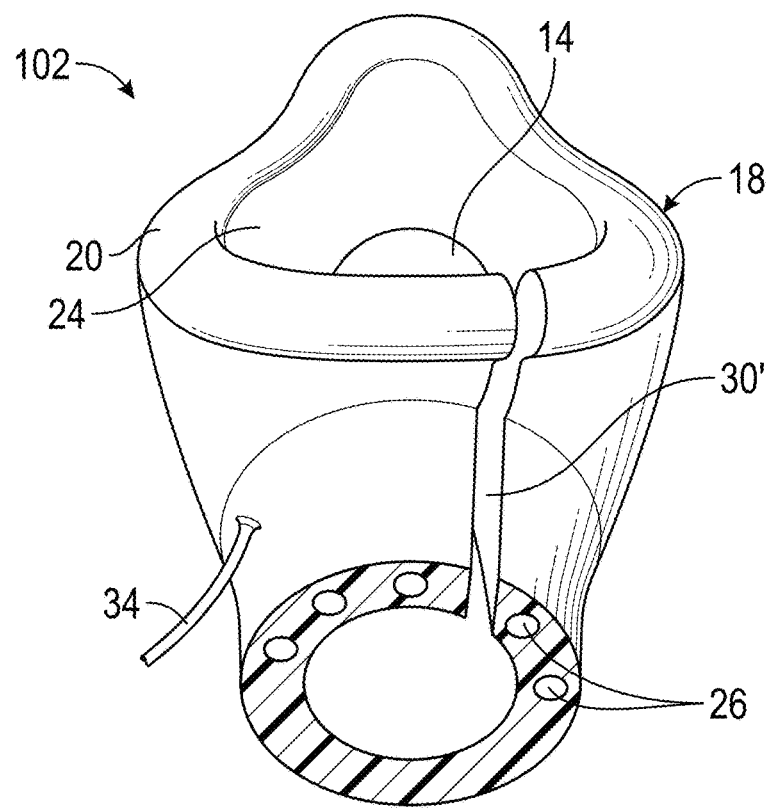
FIG. 2 is an enlarged cross-sectional view taken along the line 2-2 of FIG. 1.
Figure 5:
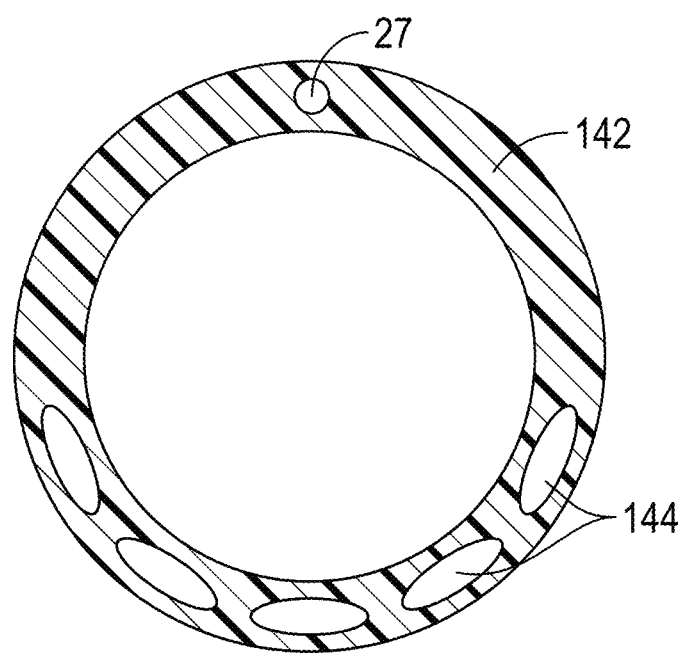
FIG. 5 is an enlarged cross-sectional view of an alternate embodiment of the SGA illustrated in FIG. 2.
Figure 6:
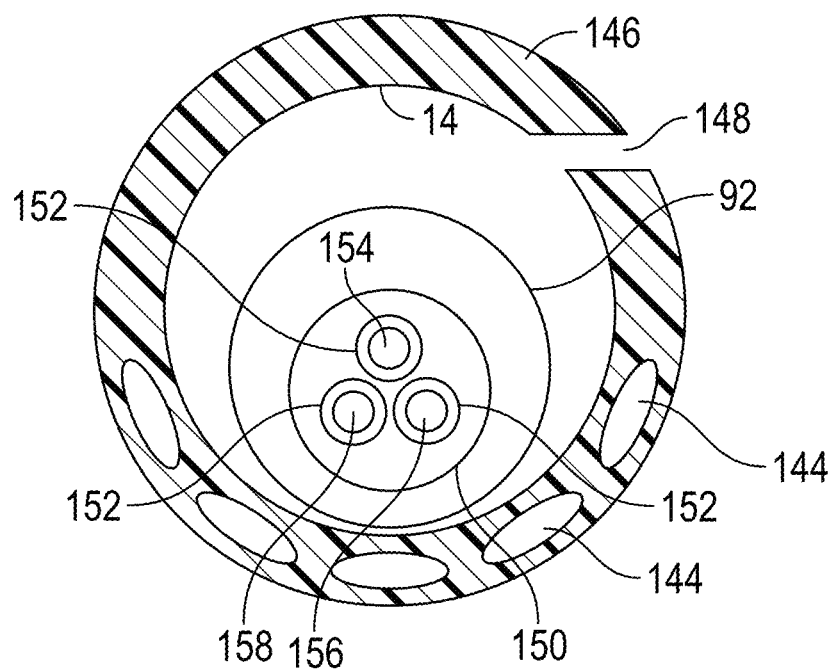
FIG. 6 is an enlarged cross-sectional view of the SGA illustrated in FIG. 5 showing the introducing stylet and the endotracheal tube therein.

FIG. 2 is an enlarged cross-sectional view of the neck 16 of an alternate embodiment of the SGA 102 showing the alternate location for the slot 30' and the closure 32', and a conventional air inflation tube 34, described below. FIG. 5 is an enlarged cross-sectional view of an alternate embodiment of the neck 142 of an SGA that is otherwise the same as the SGA 102. As shown in FIG. 5, this embodiment of the SGA 102 has a plurality of oval shaped fluid flow channels 144 and a video imaging channel 27. FIG. 6 is another alternate embodiment of the neck 146 of an SGA that is otherwise the same as the SGA 102. As shown in FIG. 6, this embodiment of the SGA 102 has the plurality of oval shaped fluid flow channels 144 and an alternate location of the sealable slot 148, shown open. FIG. 6 also includes the ETT 92 having an alternate embodiment of the introducing stylet 150 disposed therein positioned in the intubation conduit 14. The introducing stylet 150 includes longitudinally extending conduits 152. The conduits 152 are configured as, or to have mounted therein, a suction tube 154, a light source 156, and a video image device 158.

The supraglottic bowl 18 may have a non-inflatable cuff 20, such as the i-Gel® supraglottic airway manufactured by Intersurgical Ltd. The non-inflatable supraglottic cuff 20 may be formed of any gel-like or other substantially soft material designed to provide an anatomical, impression fit over the laryngeal inlet. Preferably, the shape, softness, and contours of the supraglottic cuff 20 accurately mirror the perilaryngeal anatomy. Alternatively, the supraglottic cuff 20, or any one or more portions thereof, may be inflatable and therefore include the conventional air inflation tube 34, as shown in FIG. 2. The air inflation tube 34 may be attached to the supraglottic bowl 18 and configured for attachment to a source of air, such as a syringe. Although illustrated in one location, the air inflation tube 34 may be attached to the supraglottic bowl 18 at any desired location. It will be understood that the supraglottic bowl 18 may have any desired shape, including a shape configured to displace the epiglottis and laryngeal structures to optimize the user's view of the vocal cords. Advantageously, the inflatable supraglottic cuff 20 allows the user to more easily displace laryngeal structures such as the epiglottis.

Figure 3:
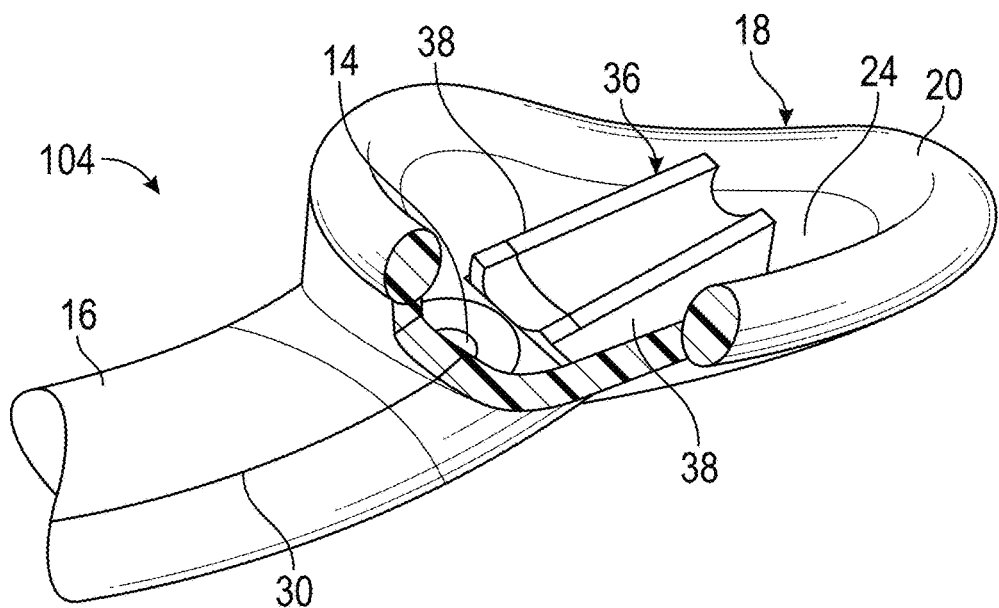
FIG. 3 is a perspective view of an alternate embodiment of the SGA illustrated in FIG. 1 showing the ramp.

Referring to FIG. 3, a perspective view of an alternate embodiment of the SGA is shown at 104 and includes the neck 16, the supraglottic bowl 18, the cuff 20, the bowl surface 24, the sealable slot 30, and the intubation conduit 14. The bowl surface 24 of the SGA 104 may include a ramp 36, to deflect the advancement of the ETT 92 more anteriorly. The ramp 36 may also have lateral walls 38 to help improve the position of the ETT 92 in the midline while advancing the ETT 92 forward toward the trachea. The ramp 36 and its walls 38 may be solid or inflatable as described above regarding the supraglottic bowl 18. It will be understood that the entire SGA 12, or any portion thereof, may be inflatable via a proximal pilot cuff (not shown) or an inflation valve port (not shown) as is known on conventional laryngeal masks, supraglottic airways and face masks. The ramp 36 and its lateral walls 38 may be articulating or elevating via a proximal lever (not shown) or a remote control mechanism (not shown). If inflatable, the pilot cuff (not shown) or inflation valve port (not shown) would be accessed on the proximal end 12B.

FIGS. 10, and 14 through 19 illustrate alternate embodiments of the SGA 12 having alternate arrangements of the fluid flow channels 26. For example, FIG. 10 is a top plan view of an alternate embodiment of the SGA 110. The SGA 110 includes the neck 16, the supraglottic bowl 18, the cuff 20, the bowl surface 24, and the intubation conduit 14. The SGA 110 also includes the video imaging device 40, an alternate embodiment of the sealable slot 126 having an overlapping air-tight closure 128, and enlarged, generally oval shaped ventilation channels 124 in the bowl surface 24.

Figure 14:
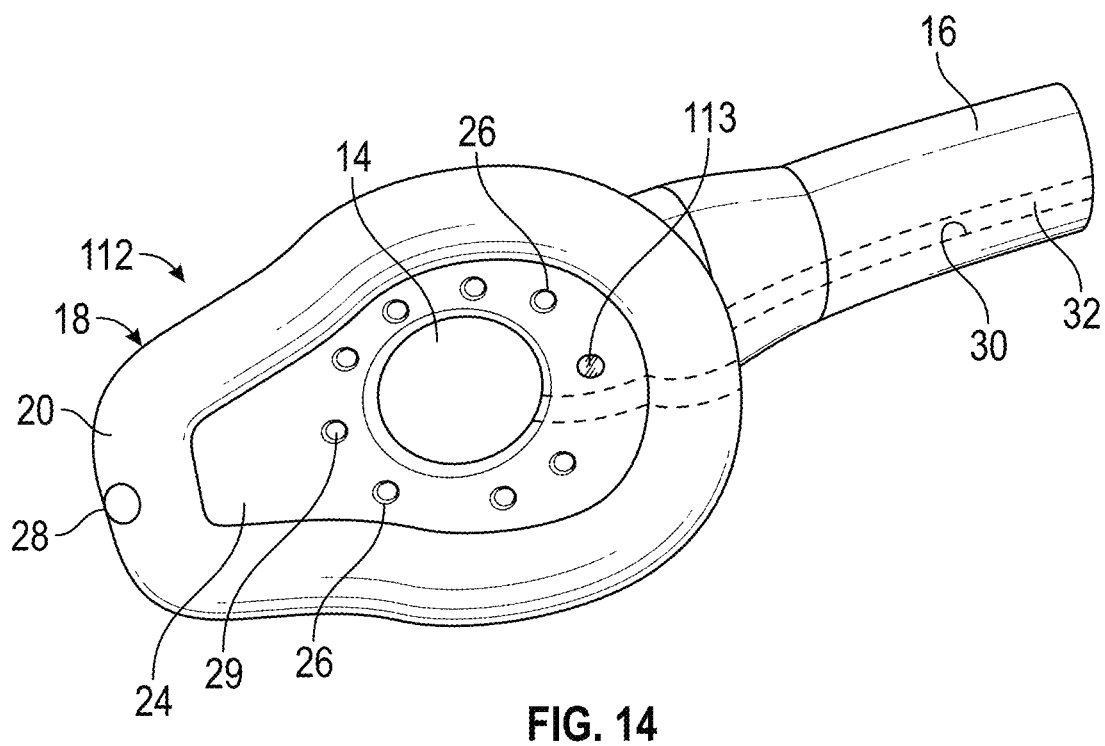
FIG. 14 is a top plan view of a portion of an alternate embodiment of the SGA illustrated in FIG. 1, showing a fifth alternate embodiment of the ventilation channels.

FIG. 14 is a top plan view of an alternate embodiment of the SGA 112. The SGA 112 includes the neck 16, the supraglottic bowl 18, the cuff 20, the bowl surface 24, the intubation conduit 14, the sealable slot 30 and air-tight closure 32 and the gastric suction channel 28. The SGA 112 also includes an alternate embodiment of the ventilation channels 26, wherein the ventilation channels 26 are formed around the circumference of the opening of the intubation conduit 14 in the bowl surface 24. It will be understood that any number, and any arrangement in the bowl surface 24, of the ventilation channels 26 may be provided. The illustrated SGA 112 also includes a normally closed one-way valve 113 covering a channel 26 configured to receive an elongated video imaging device (not shown), and that allows forward or distal passage of the elongated video imaging device (not shown) that may be extended through the channel 26. The one-way valve 113 occluded or closed when the video imaging device (not shown) is not used, due to positive pressure on a distal (tracheal) surface of the one-way valve 113 during ventilation.

Figure 15:
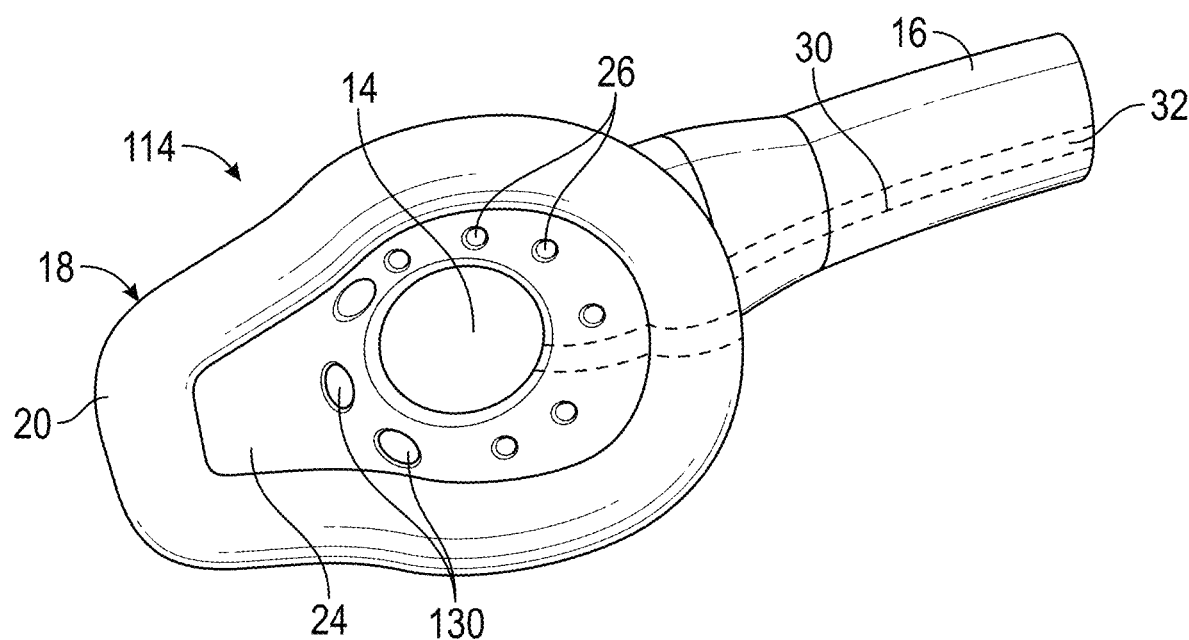
FIG. 15 is a top plan view of a portion of an alternate embodiment of the SGA illustrated in FIG. 1, showing a sixth alternate embodiment of the ventilation channels.

FIG. 15 is a top plan view of an alternate embodiment of the SGA 114. The SGA 114 is substantially the same at the SGA 112 illustrated in FIG. 14, and also includes a plurality of the ventilation channels formed around the circumference of the opening of the intubation conduit 14 in the bowl surface 24. In the SGA 114 however, the ventilation channels include the circular ventilation channels 26 and substantially oval shaped ventilation channels 130 that extend through the wall of the neck 16 and to the proximal end thereof. It will be understood that any number, combination, and arrangement in the bowl surface 24, of the ventilation channels 26 and 130 may be provided.

Figure 16:
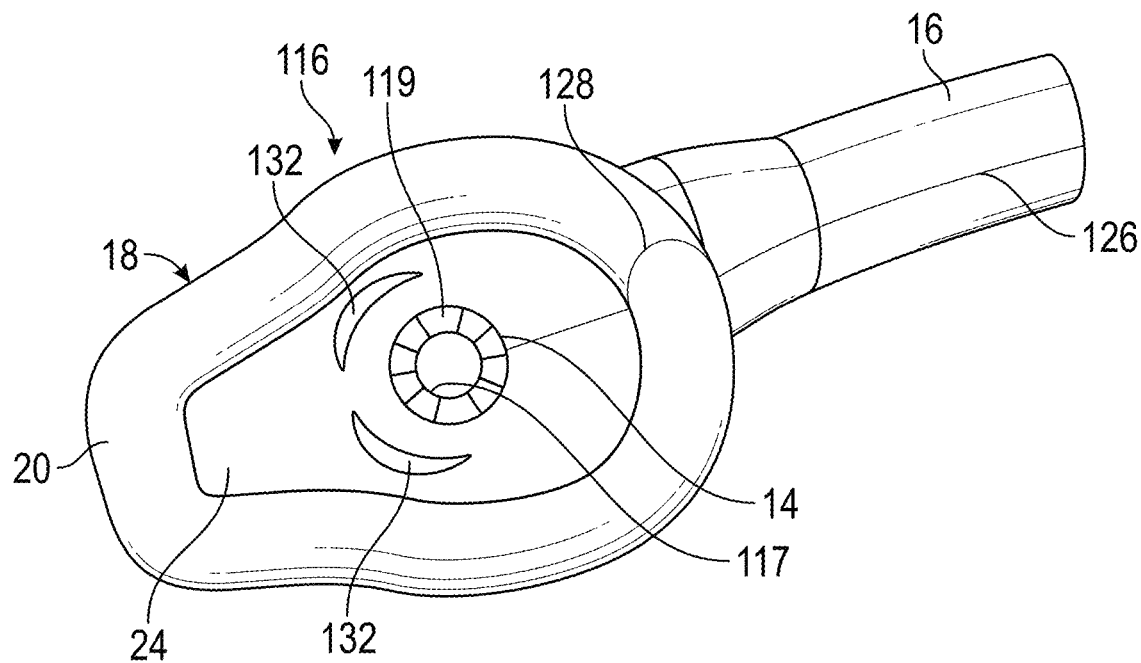
FIG. 16 is a top plan view of a portion of an alternate embodiment of the SGA illustrated in FIG. 1, showing a seventh alternate embodiment of the ventilation channels.

FIG. 16 is a top plan view of an alternate embodiment of the SGA 116. The SGA 116 is similar to the SGA 110 illustrated in FIG. 10, and includes the neck 16, the supraglottic bowl 18, the cuff 20, the bowl surface 24, the intubation conduit 14, and the sealable slot 126 having the overlapping air-tight closure 128 configuration. The SGA 116 also includes generally crescent shaped ventilation channels 132 in the bowl surface 24 that extend through the wall of the neck 16 and to the proximal end thereof. The SGA 116 further includes a distal sealing aperture 117 having a flexible, expandable collar 119. The aperture 117 of the flexible, expandable collar 119 has a diameter slightly smaller than an outside diameter of the ETT 92 or the introducing stylet 90 that will be inserted therethrough and defines an expandable aperture within the bowl surface 24. Thus, when urged through the aperture 117, the ETT 92 or the introducing stylet 90 causes the expandable collar 119 to stretch open as an inside wall of the aperture 117 of the expandable collar 119 engages and maintains an airtight seal around the ETT 92 or the introducing stylet 90 to prevent gas leakage during ventilation via fluid flow channels, such as the ventilation channels 132. It will be understood that any sealable slot, such as the slot 126, formed in the SGA 116 may also be formed in the expandable collar 119.

FIG. 17 is a top plan view of an alternate embodiment of the SGA 118. The SGA 118 includes the neck 16, the supraglottic bowl 18, the cuff 20, the bowl surface 24, and the sealable slot 30 and air-tight closure 32. The SGA 118 also includes alternate embodiments of the intubation conduit and the ventilation channel. As shown in FIG. 17, the intubation conduit 133 and a ventilation channel 134 are parallel or collaterally arranged, separated by a wall 135, and extend longitudinally through the SGA 118 from a proximal end of the neck 16 to an opening in the bowl surface.

Figure 18:
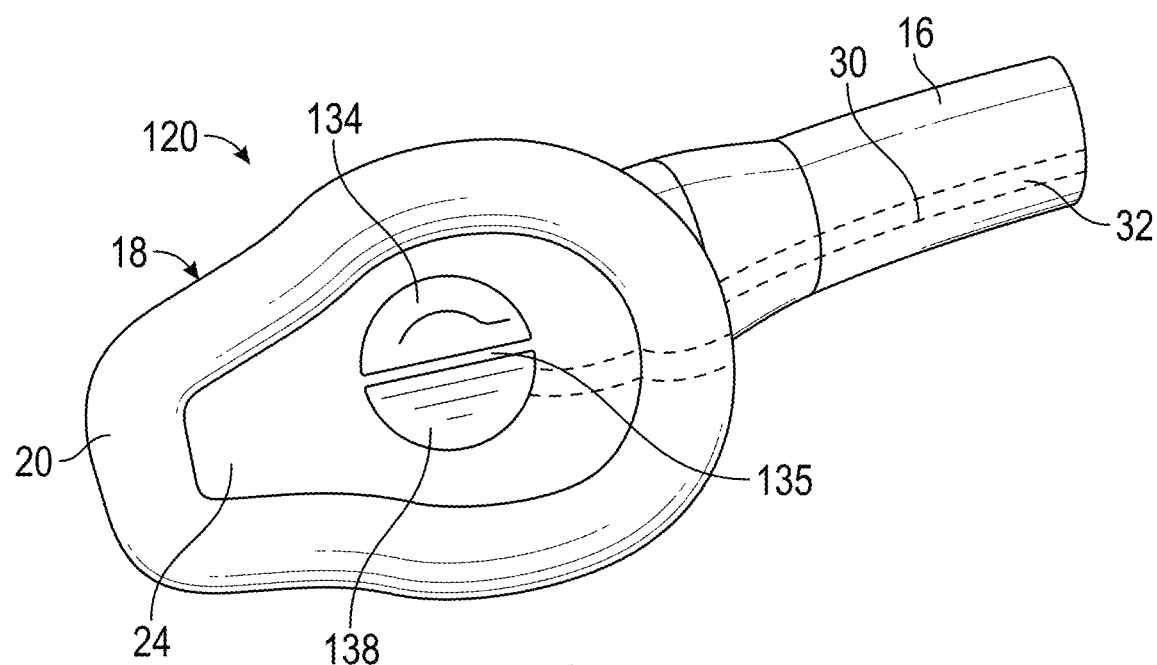
FIG. 18 is a top plan view of a portion of an alternate embodiment of the SGA illustrated in FIG. 17, showing a first embodiment of the one-way valve door in a closed position.

FIG. 18 is a top plan view of an alternate embodiment of the SGA 120. The SGA 120 is similar to the SGA 118 illustrated in FIG. 17, but additionally includes a first embodiment of a normally closed one-way door or valve 138 covering the opening of the intubation conduit 133, and shown in a closed position.

Figure 19:
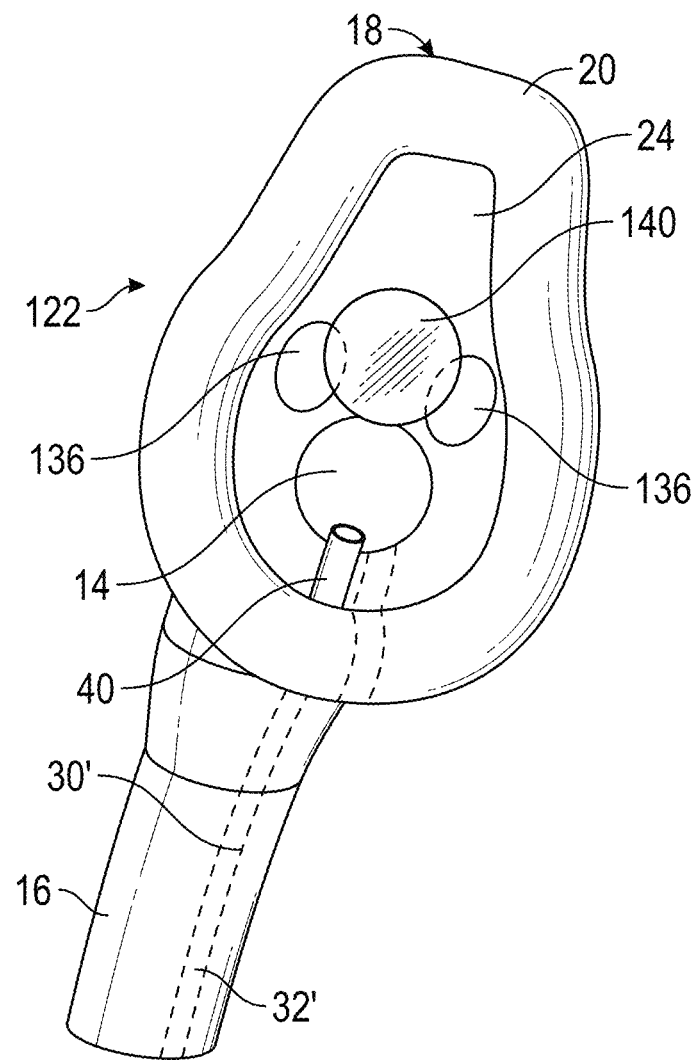
FIG. 19 is a top plan view of a portion of an alternate embodiment of the SGA illustrated in FIG. 1, showing the protruding video imaging device or channel, a ninth alternate embodiment of the ventilation channels, and a second embodiment of the one-way valve door in a fully open position for clarity.

FIG. 19 is a top plan view of an alternate embodiment of the SGA 122. The SGA 122 includes the neck 16, the supraglottic bowl 18, the cuff 20, the bowl surface 24, and the intubation conduit 14. The SGA 124 also includes the video imaging device 40, the alternate slot 30' and closure 32', and enlarged, generally oval shaped ventilation channels 136 in the bowl surface 24. The SGA 122 additionally includes a second embodiment of the normally closed one-way door or valve 140 covering the intubation conduit 14, and shown in a fully open position for clarity.

Figure 7:
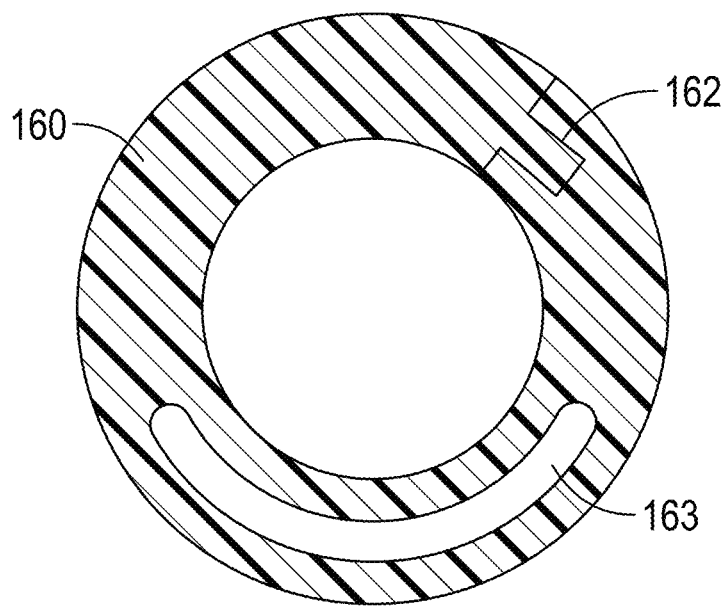
FIG. 7 is an enlarged cross-sectional view of an alternate embodiment of the neck of the SGA showing one embodiment of the sealable slot and a first alternate embodiment of the ventilation channel.
Figure 9:
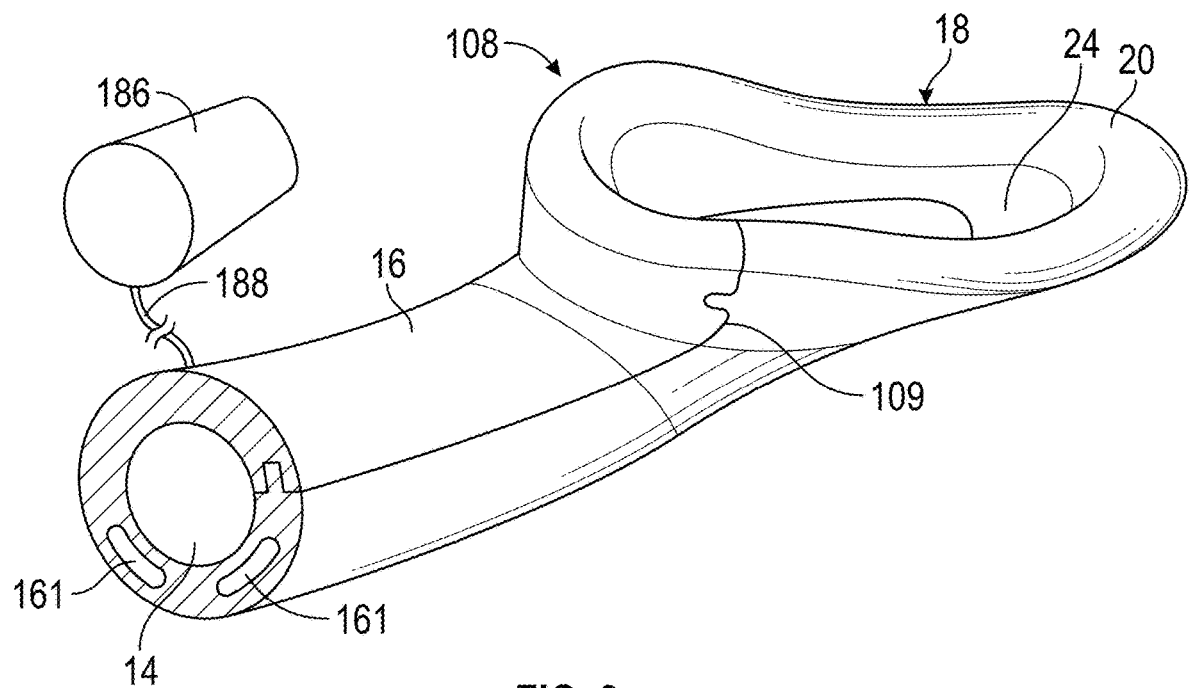
FIG. 9 is a perspective view of a portion of the SGA showing a third embodiment of the sealable slot.

In addition to the closures 32 and 32' in FIG. 1, the closure 14 in FIG. 6, the closure 109 in FIG. 9, and the closure 128 in FIGS. 10 and 16, other types of re-sealable closures may be used. For example, the various embodiments of the SGA disclosed herein may include an occluding, interlocking closure 162 as shown in the alternate embodiment of the neck 160 in FIG. 7. The neck 160 is a component of an SGA that is otherwise the same as the SGA 102. As shown in FIG. 7, this embodiment of the SGA 102 also has an elongated, arcuate ventilation channel 163. Other than its shape and size, the ventilation channel 163 is otherwise the same as the ventilation channels 26 described herein above. It will be understood that any of the embodiments of the SGAs described herein may have any one or more of the ventilation channels described herein, including the ventilation channel 163.

Figure 8:
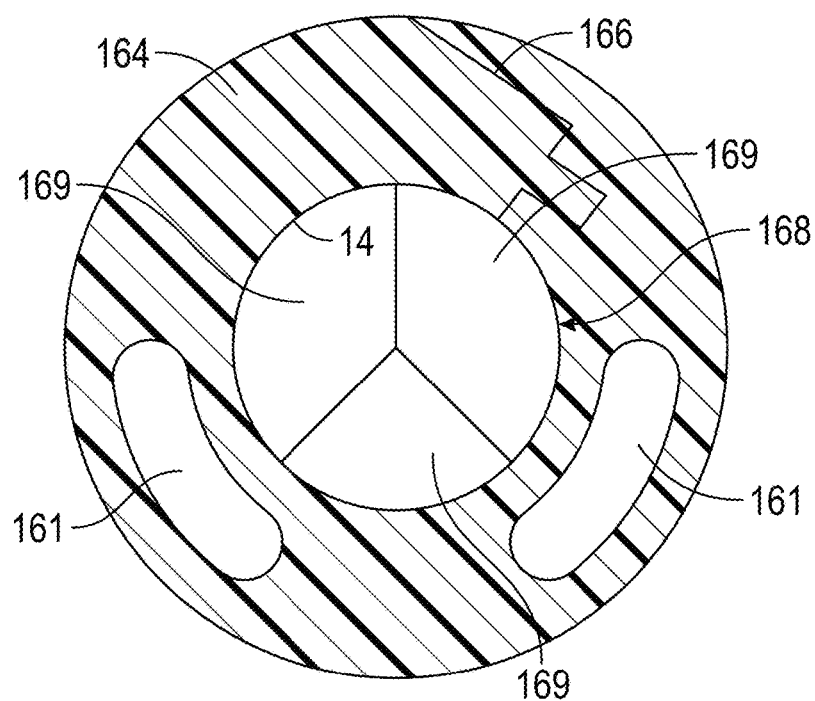
FIG. 8 is an enlarged cross-sectional view of an alternate embodiment of the neck of the SGA showing a second embodiment of the sealable slot, a second embodiment of the one-way valve, and a second alternate embodiment of the ventilation channels.
Figure 11:
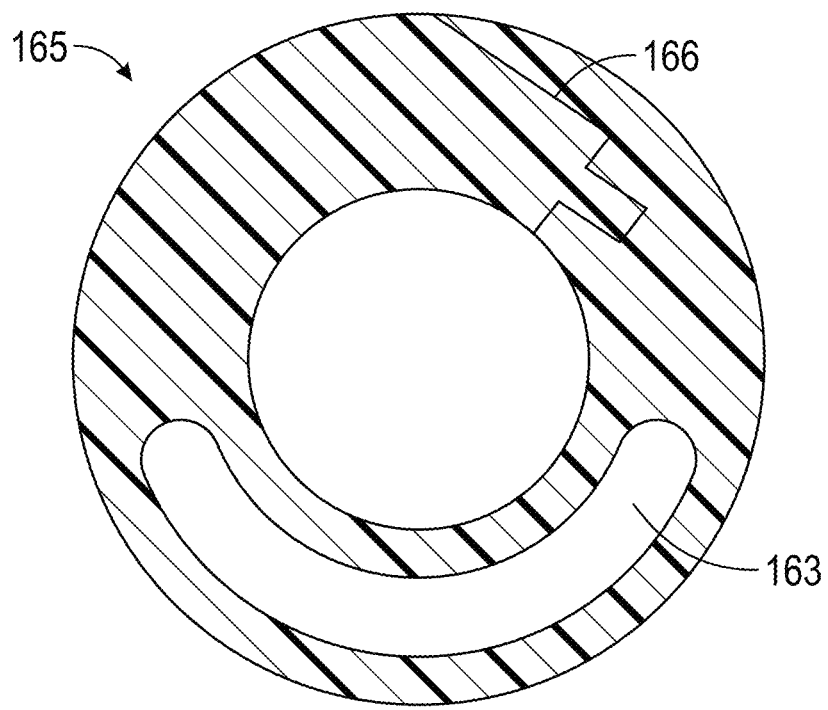
FIG. 11 is an enlarged cross-sectional view of an alternate embodiment of the neck of the SGA showing the sealable slot illustrated in FIG. 8 and the elongated, arcuate ventilation channel.

An overlapping, occluding, and interlocking closure 166 is shown in the alternate embodiment of the neck 164 in FIG. 8 and the neck 165 in FIG. 11. The neck 164 in FIG. 8 is a component of an SGA that is otherwise the same as the SGA 102. As shown in FIG. 8, this embodiment of the SGA 102 also has an embodiment of a one-way valve 168 having three overlapping leaves 169, the purpose for which is described below, and two elongated ventilation channels 161. The one-way valve 168 is preferably positioned at the distal end of the intubation conduit 14, but may be positioned at any desired location within the intubation conduit 14. The neck 165 in FIG. 11 is a component of an SGA that is otherwise the same as the SGA 102. As shown in FIG. 11, this embodiment of the SGA 102 also has the ventilation channel 163.

FIG. 9 shows another embodiment of the SGA 108 having an overlapping, interlocking closure 109, and the two elongated ventilation channels 161. Also illustrated in FIG. 9 is a plug 186. The plug 186 may be attached to the neck 16 by a flexible connector 188. The plug 186 is configured to be inserted into the intubation conduit 14 at the proximal end 12B of the SGA 108 and to define a fluid-tight seal therein.

Figure 9A:
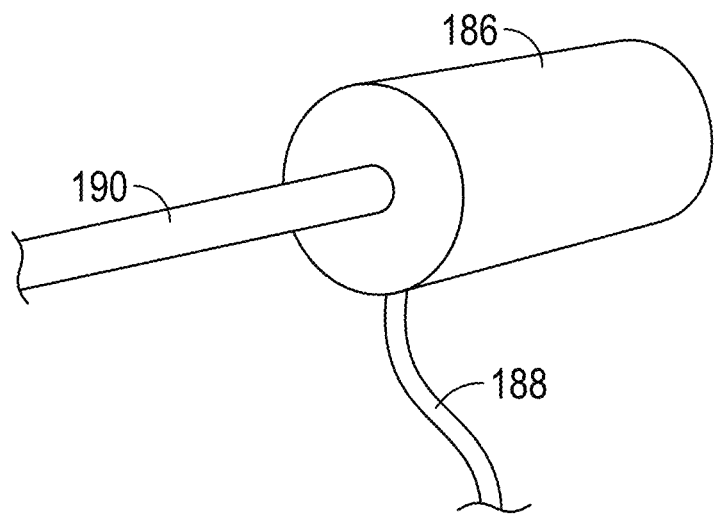
FIG. 9A is a perspective view of an alternate embodiment of the plug illustrated in FIG. 9.

Thus, the plug 186 may be inserted into and close the intubation conduit 14 when desired. As shown in FIG. 9A, the plug 186 may include a longitudinally extending elongated stem 190 to aid the user in positioning the plug 186 at any desired location in the intubation conduit 14, including the distal end thereof, the proximal end thereof, and any position intermediate the proximal and distal ends of the intubation conduit 14.

Figure 12:
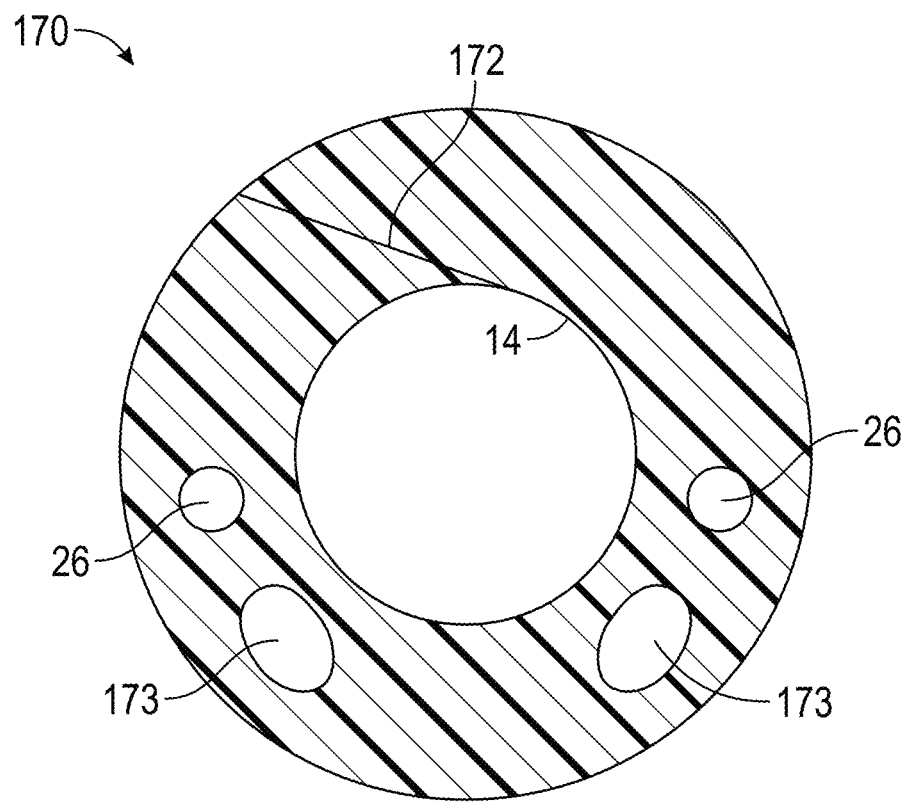
FIG. 12 is an enlarged cross-sectional view of an alternate embodiment of the neck of the SGA showing a fifth embodiment of the sealable slot and a fourth alternate embodiment of the ventilation channels.

An overlapping, occluding closure 172 is shown in the alternate embodiment of the neck 170 in FIG. 12. The neck 170 in FIG. 12 is a component of an SGA that is otherwise the same as the SGA 102. As shown in FIG. 12, this embodiment of the SGA 102 also has a plurality of the ventilation channels 26 and a plurality of oval shaped fluid flow channels 173. It will be understood that any of the embodiments of the SGAs described herein may have any one of the embodiments of the closures described herein.

Additionally, the cuff 20 of the supraglottic bowl 18 may have a split formed therein such that at the split, the two cuff surfaces may meet in a tangential fashion to improve the temporary occlusion of the split. Other interlocking or snap fit closure features may be provided to occlude the split. The slot 30, when open, allows the SGA 12 to be removed from around the ETT 92 after the ETT 92 is placed in the trachea but allows the cuff 20 of the supraglottic bowl 18 to maintain a tight cuff seal for ventilation.

The supraglottic bowl 18 is configured to seal the periglottic area to ensure that all air, gas, or oxygen flows into the trachea and not into the esophagus or leak back into the atmosphere.

The intubation conduit 14 may be formed with a normally closed one-way valve that allows forward or distal passage of the ETT 92 through the intubation conduit 14 and the one-way valve toward the trachea, but is occluded or closed when ventilating through the fluid flow channels 26 due to positive pressure on a distal (tracheal) surface of the one-way valve during ventilation. One example of such a one-way valve is the one-way valve 168 shown in FIG. 8 that is similar to an aortic valve. Another example of the one-way valve is the normally closed one-way valve 140, as shown in FIG. 19. An additional example of the one-way valve is the normally closed one-way valve 138 shown in FIG. 18. It will be understood that the one-way valves 138, 140, and 168 may be formed at the proximal end of the intubation conduit 14, the distal end of the intubation conduit 14, or at any other desired location within the intubation conduit 14.

If desired, the intubation conduit 14 may be formed having one or more reduced diameter portions (not shown) along the length of the intubation conduit 14. This reduced diameter portion or portions has a diameter slightly smaller than an outside diameter of the ETT 92 or the introducing stylet 90 that will be inserted therethrough and defines an expandable aperture within the intubation conduit 14. Thus, when urged through the reduced diameter portion, the ETT 92 or the introducing stylet 90 causes the expandable aperture to stretch open as an inside wall of the expandable aperture engages and maintains an airtight seal around the ETT 92 or the introducing stylet 90 to prevent gas leakage during ventilation via fluid flow channels, such as the fluid flow channels 26 configured as ventilation channels. It will be understood that any sealable slot 30 formed in the SGA 12 will also be formed in the reduced diameter portion.

Figure 13:
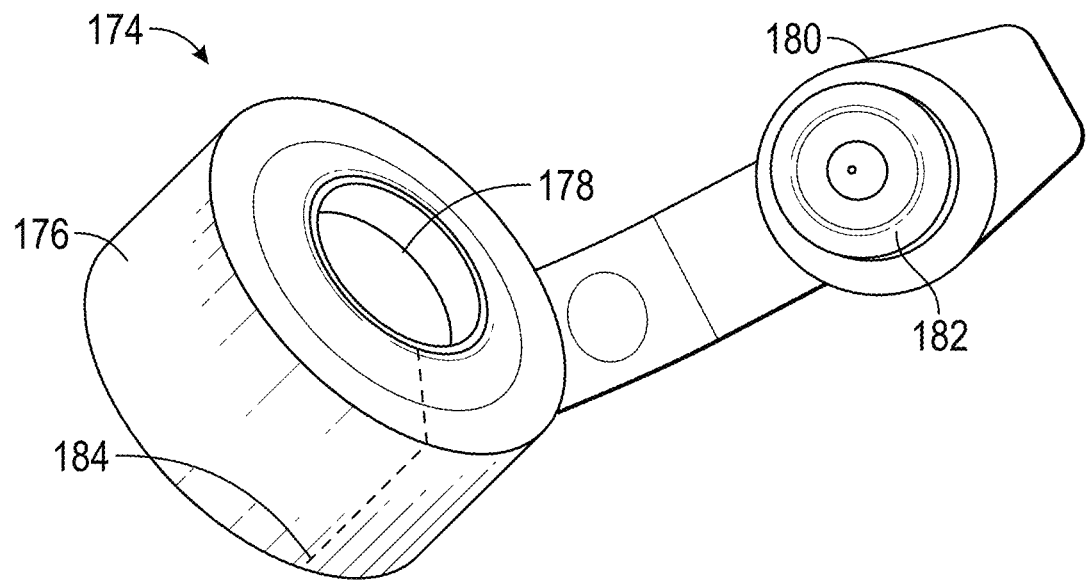
FIG. 13 is a perspective view of the cap.

The proximal end 12B of the SGA 12 may have a cap 174 attached thereto, as shown in FIG. 13. The illustrated cap 174 includes a body 176 having an aperture 178 formed therethrough and a closure 180 movably attached to the body 176, wherein the body 176 is configured to attach to, or be formed on, the proximal end 12B of the SGA 12. Like the reduced diameter portion of the intubation conduit 14 described above, the aperture 178 may have a diameter slightly smaller than an outside diameter of the ETT 92 that will be inserted therethrough and is expandable. Thus, when urged through the aperture 178, the ETT 92 causes the aperture 178 to stretch open as an inside wall thereof engages and maintains an airtight seal around the ETT 92 to prevent gas leakage during ventilation via the fluid flow channels 26 configured as ventilation channels. The closure 180 includes a protrusion or closure plug 182 that is configured to be inserted into and close the aperture 178 when it desired to have the proximal end 12B closed. The cap 174 may be removable, or may have a sealable slot 184 formed therein, wherein the sealable slot 184 is similar to and preferably aligned with the sealable slot 30.

It will be further understood that the SGA 12 may be formed with any combination of one or more of the expandable collar 119, the normally closed one-way valves 138, 140, and 168, the plug 186, the cap 174, and/or the reduced diameter portions that define expandable apertures that are configured to prevent retrograde air or fluid passage during ventilation through the ventilation channel or channels 26. As used herein, these features (i.e., the expandable collar 119, the normally closed one-way valves 138, 140, and 168, the plug 186, the cap 174, and the reduced diameter portions that define expandable apertures) may be collectively referred to as intubation conduit occluding features.

Although the longitudinally extending intubation conduit 14 has been described herein as being configured for the introduction of the ETT 92 into the patient, it will be understood the conduit 14 may, if desired, function as a working channel for instruments associated with a variety of medical procedures, including but not limited to bronchoscopy, laryngoscopy, vocal cord examination, vocal cord procedures, and the like.

Figure 20:
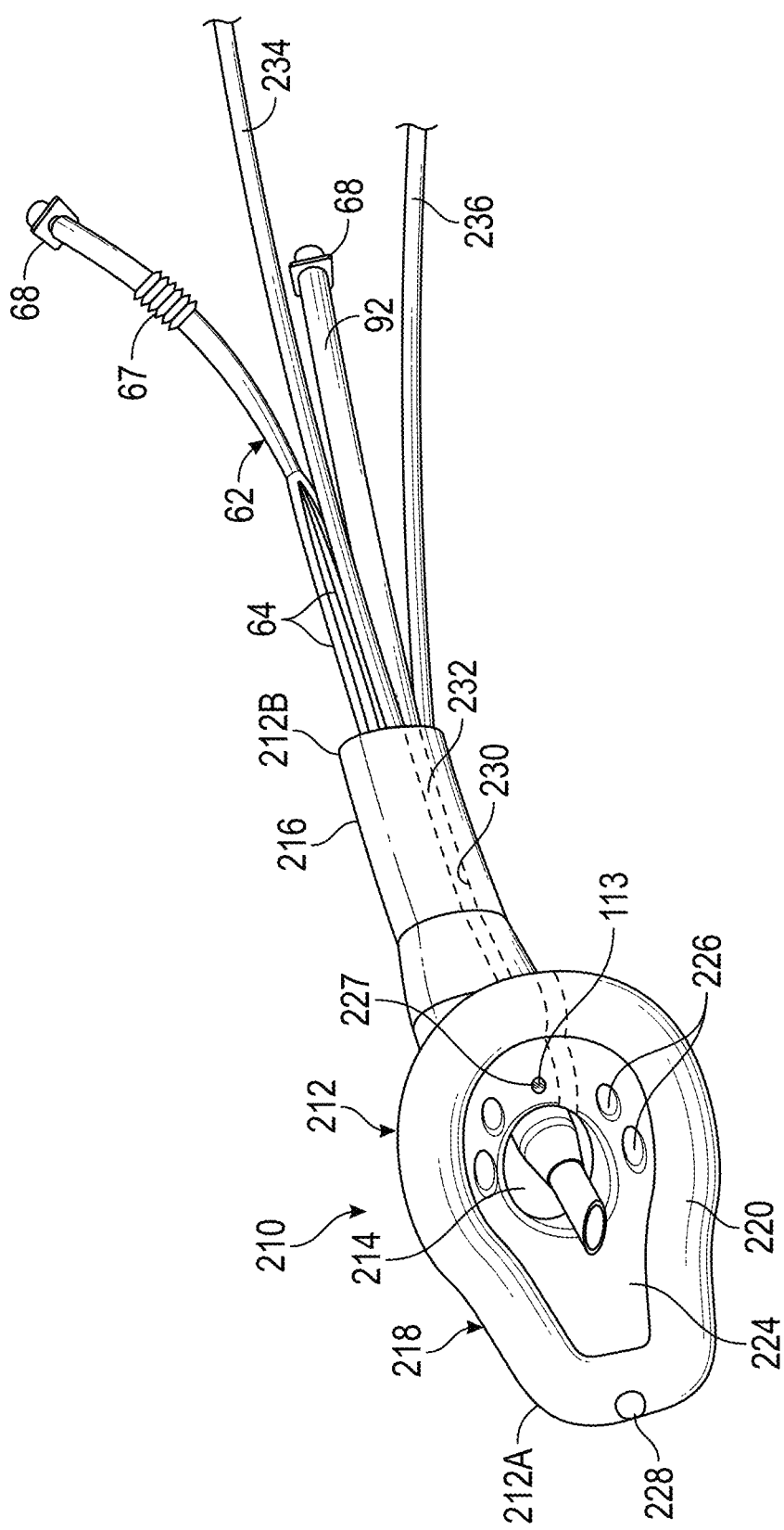
FIG. 20 is a perspective view of a second embodiment of the improved supraglottic airway assembly illustrated in FIG. 1.

FIG. 20 is a perspective view of a second embodiment of the improved SGA assembly illustrated in FIG. 1 and shown generally at 210. The SGA assembly 210 includes the introducing stylet 90 (not shown in FIG. 20) with the ETT 92 mounted thereon extending through the SGA assembly 210. Like the SGA assembly 10, the SGA assembly 210 is configured to ventilate and have the ETT 92 carried therein such that a patient may be simultaneously ventilated and intubated. The SGA assembly 210 includes the SGA 212 having the distal end 12A, the proximal end 212B, and the longitudinally extending intubation conduit 214 formed therethrough.

The SGA 212 includes the elongated neck 216 formed at the proximal end 212B thereof and the supraglottic bowl 218 formed at the distal end 212A thereof and extending from the neck 216. The supraglottic bowl 218 includes the cuff 220 and defines the bowl surface 224. A plurality of the fluid flow channels 226 may be formed longitudinally through the neck 216 to the bowl surface 224. In FIG. 20 four such fluid flow channels 226 are illustrated, however any desired number of fluid flow channels 226 may be formed in the SGA 212. One or more of the fluid flow channels 226 are configured as ventilation channels that advantageously allow for patient ventilation simultaneously with, and independent of patient intubation.

Additionally, one of the fluid flow channels may be configured as a video imaging channel 227, the opening of which may include the normally closed one-way valve 113 described above. Further, the SGA 212 may include the gastric suction channel 228 formed longitudinally through the neck 216 to the distal end 212A of the cuff 220 of the bowl 218. The SGA assembly 210 also includes the sealable slot 230 having the elongated, air-tight closure 232. Like the sealable slot 30, the sealable slot 230 is formed along the entire length of the intubation conduit 214, from the proximal end 212B of the neck 216 to the opening of the intubation conduit 214 in the bowl surface 224 and continuously through the bowl surface 224 and the cuff 220 of the supraglottic bowl 218.

The tube assembly 62 extends outwardly from the proximal end 212B of the SGA 212 and includes a plurality of the first fluid flow tubes 64, the proximal ends of which merge into the single second fluid flow tube 66. The conventional 15 mm connector 68 is attached to the proximal end of the second fluid flow tube 66. A video line 234 may be connected to a video imaging device (not shown), extends outwardly from the video imaging channel 227 at the proximal end 212B of the SGA 212, and may be operationally connected, for example wired or wirelessly connected, to a monitor, such as the video monitor 98. A gastric suction tube 236 extends outwardly from the gastric suction channel 228 at the proximal end 212B of the SGA 212, and may be operationally connected to a source of suction (not shown).

The principle and mode of operation of this invention have been explained and illustrated in its preferred embodiments. However, it must be understood that this invention may be practiced otherwise than as specifically explained and illustrated without departing from its spirit or scope.

What is claimed is:

1. A bi-functional intubating and ventilating supraglottic airway comprising:
   a supraglottic bowl defining a distal end, a neck extending outward of the supraglottic bowl and defining a proximal end, a longitudinally extending intubation conduit formed therethrough, the supraglottic bowl including a cuff and defining a bowl surface, wherein the intubation conduit extends from the proximal end of the neck to an opening in the bowl surface, and wherein the intubation conduit is configured to have an endotracheal tube (ETT) inserted therethrough;
   at least one fluid flow channel formed longitudinally through a wall of the supraglottic airway, collaterally to the intubation conduit and from the proximal end to the bowl surface within the supraglottic bowl;
   wherein the at least one fluid flow channel is configured as a ventilation channel for the flow of air from the proximal end to the supraglottic bowl;
   wherein the supraglottic airway further includes a fluid flow tube connected within the ventilation channel, and a 15 mm connector at a proximal end of the fluid flow tube; and
   a connector configured to releasably connect the fluid flow tube to one of the ETT and an introducing stylet upon which the ETT is positioned.

2. The bi-functional intubating and ventilating supraglottic airway according to claim 1, further including an intubation conduit occluding feature.

3. The bi-functional intubating and ventilating supraglottic airway according to claim 2, further including a sealable slot extending along an entire length of the intubation conduit, the sealable slot extending through the neck, the cuff, and the bowl surface.

4. The bi-functional intubating and ventilating supraglottic airway according to claim 2, further including a plug attached to the proximal end of the neck, the plug configured to be inserted into the intubation conduit at the proximal end of the neck and to define a fluid-tight seal therein.

5. The bi-functional intubating and ventilating supraglottic airway according to claim 4, wherein the plug includes a longitudinally extending elongated stem configured to allow the plug to be urged into and positioned at any desired location within the intubation conduit.

6. The bi-functional intubating and ventilating supraglottic airway according to claim 2, further including a normally closed one-way valve within the intubation conduit, the one-way valve configured to allow distal passage of one of the ETT and an introducing stylet upon which the ETT may be mounted, through the intubation conduit, and further configured to occlude the intubation conduit during ventilating through the fluid flow channel, wherein the normally closed one-way valve is formed at one of a distal end of the intubation conduit, a proximal end of the intubation conduit, and a location intermediate the distal end and the proximal end of the intubation conduit.

7. The bi-functional intubating and ventilating supraglottic airway according to claim 2, further including a cap attached to the proximal end of the neck, the cap including a body having an aperture formed therethrough and a closure movably attached to the body and configured to close the aperture of the body.

8. The bi-functional intubating and ventilating supraglottic airway according to claim 7, wherein the aperture has a diameter slightly smaller than an outside diameter of one of the ETT and an introducing stylet upon which the ETT may be mounted that will be inserted therethrough, and is expandable, and wherein the expandable aperture is configured to engage and maintains an airtight seal around the one of the ETT and an introducing stylet inserted therethrough to prevent gas leakage during ventilation via the fluid flow channel.

9. The bi-functional intubating and ventilating supraglottic airway according to claim 8, wherein the cap includes a sealable slot formed therein and aligned with the sealable slot of the supraglottic airway.

10. The bi-functional intubating and ventilating supraglottic airway according to claim 2, further including a reduced diameter portion within the intubation conduit, wherein the reduced diameter portion has a diameter slightly smaller than an outside diameter of one of the ETT that will be inserted therethrough and an introducing stylet upon which the ETT may be mounted, and defines an expandable aperture within the intubation conduit, and wherein the expandable aperture is configured to stretch open as an inside wall of the expandable aperture engages and maintains an airtight seal around the one of the ETT and the introducing stylet during ventilation of air via the fluid flow channels.

11. The bi-functional intubating and ventilating supraglottic airway according to claim 2, further including a sealing aperture having a flexible, expandable collar within the intubation conduit, the flexible, expandable collar configured to allow distal passage of one of the ETT and an introducing stylet upon which the ETT may be mounted, through the intubation conduit, and further configured to occlude the intubation conduit during ventilating through the ventilation channel, wherein the flexible, expandable collar is formed at one of a distal end of the intubation conduit, a proximal end of the intubation conduit, and a location intermediate the distal end and the proximal end of the intubation conduit.

12. The bi-functional intubating and ventilating supraglottic airway according to claim 1, further including a sealable slot having a first portion along a length of the intubation conduit in the neck, and a second portion along a length of the intubation conduit in the bowl surface, the sealable slot not formed in the cuff.

13. The bi-functional intubating and ventilating supraglottic airway according to claim 12, wherein the cuff is formed from expandable, stretchable material.

14. The bi-functional intubating and ventilating supraglottic airway according to claim 1, further including a gastric suction channel formed longitudinally through the wall of the supraglottic airway from the proximal end of the neck to a distal end of the cuff of the bowl.

15. The bi-functional intubating and ventilating supraglottic airway according to claim 1, further including split-capable feature extending along an entire length of the intubation conduit, the split-capable feature extending through the neck, the cuff, and the bowl surface, wherein the split capable feature includes one or more cuts along a line that defines a location for a slot, the cuts penetrating through only a portion of a thickness of a wall of the supraglottic airway, such that the split capable feature is airtight and un-opened until urged open by a user to define the slot.

16. The bi-functional intubating and ventilating supraglottic airway according to claim 3, wherein the sealable slot includes an air-tight closure along its length.

17. The bi-functional intubating and ventilating supraglottic airway according to claim 16, wherein the air-tight closure is one of overlapping, overlapping and occluding, overlapping and interlocking, and overlapping, occluding and interlocking.

18. The bi-functional intubating and ventilating supraglottic airway according to claim 1, further including a video imaging channel formed longitudinally through the wall of the supraglottic airway from the proximal end of the neck to the bowl surface, the video imaging channel having a video imaging device mounted therein.

19. The bi-functional intubating and ventilating supraglottic airway according to claim 18, wherein a portion of the video imaging channel extends outwardly of the bowl surface into the supraglottic bowl.

20. The bi-functional intubating and ventilating supraglottic airway according to claim 19, wherein the portion of the video imaging channel that extends outward of the bowl surface into the supraglottic bowl is configured to be one of articulated and formed from malleable material.

21. The bi-functional intubating and ventilating supraglottic airway according to claim 1, wherein the supraglottic airway includes a ramp formed in the bowl surface, the ramp configured to deflect the advancement of the ETT anteriorly.

22. The bi-functional intubating and ventilating supraglottic airway according to claim 21, wherein the ramp is one of inflatable, articulating, and elevating.

23. The bi-functional intubating and ventilating supraglottic airway according to claim 1, wherein the connector is configured as one of a rigid, fixed, telescoping, foldable, and hinged connector that is further configured to allow the user to change a relative distance between the second fluid flow tube and the ETT.

24. A bi-functional intubating and ventilating supraglottic airway comprising:
    a supraglottic bowl defining a distal end, a neck extending outward of the supraglottic bowl and defining a proximal end, a longitudinally extending intubation conduit formed therethrough, the supraglottic bowl including a cuff and defining a bowl surface, wherein the intubation conduit extends from the proximal end of the neck to an opening in the bowl surface, and wherein the intubation conduit is configured to have an endotracheal tube (ETT) inserted therethrough, and a plurality of fluid flow channels formed longitudinally through a wall of the supraglottic airway from the proximal end to the bowl surface within the supraglottic bowl;

wherein one or more of the fluid flow channels are configured as ventilation channels that allow for patient ventilation simultaneously with, and independent of patient intubation;

an intubation conduit occluding feature;

a sealable slot having an elongated, air-tight closure;

a tube assembly extending outwardly from the proximal end of the supraglottic airway, the tube assembly including a plurality of first fluid flow tubes, the distal ends of which are connected within the fluid flow channels, the proximal ends of which merge into a single second fluid flow tube, and a 15 mm connector at the proximal end of the second fluid flow tube; and a connector configured to releasably connect the second fluid flow tube to the ETT.

25. The bi-functional intubating and ventilating supraglottic airway according to claim 24, wherein the intubation conduit occluding feature is one of a plug attached to the proximal end of the neck, the plug configured to be inserted into the intubation conduit at the proximal end of the neck and to define a fluid-tight seal therein, a cap attached to the proximal end of the neck, the cap including a body having an aperture formed therethrough and a closure movably attached to the body and configured to close the aperture of the body, a reduced diameter portion within the intubation conduit, wherein the reduced diameter portion has a diameter slightly smaller than an outside diameter of one of the ETT and the introducing stylet, the reduced diameter portion defining an expandable aperture within the intubation conduit, a normally closed one-way valve within the intubation conduit, the one-way valve configured to allow distal passage of one of the ETT and an introducing stylet upon which the ETT may be mounted, through the intubation conduit, and a sealing aperture having a flexible, expandable collar within the intubation conduit, the flexible, expandable collar configured to allow distal passage of one of the ETT and the introducing stylet upon which the ETT may be mounted, through the intubation conduit.

26. A bi-functional intubating and ventilating supraglottic airway comprising:

a supraglottic bowl defining a distal end, a neck extending outward of the supraglottic bowl and defining a proximal end, a longitudinally extending intubation conduit formed therethrough, the supraglottic bowl including a cuff and defining a bowl surface, wherein the intubation conduit extends from the proximal end of the neck to an opening in the bowl surface, and wherein the intubation conduit is configured to have an endotracheal tube (ETT) inserted therethrough;

a plurality of ventilation channels formed longitudinally through a wall of the supraglottic airway from the proximal end to the bowl surface within the supraglottic bowl;

a sealable slot extending along an entire length of the intubation conduit, the sealable slot extending through the neck, the cuff, and the bowl surface;

an air-tight closure along the length of the sealable slot;

a gastric suction channel formed longitudinally through the wall of the supraglottic airway from the proximal end of the neck to a distal end of the cuff of the bowl; and a video imaging channel formed longitudinally through the wall of the supraglottic airway from the proximal end of the neck to the bowl surface, the video imaging channel having a video imaging device mounted therein;

wherein the air-tight closure is one of overlapping, overlapping and occluding, overlapping and interlocking, and overlapping, occluding and interlocking, and wherein the supraglottic airway further includes:

a tube assembly extending outwardly from the proximal end of the supraglottic airway, the tube assembly including a plurality of first fluid flow tubes, the proximal ends of which merge into a single second fluid flow tube and a 15 mm connector at the proximal end of the second fluid flow tube;

a video line connected to a video imaging device and extending outwardly from the video imaging channel at the proximal end of the supraglottic airway; and a connector configured to releasably connect the second fluid flow tube to the ETT.

27. A bi-functional intubating and ventilating supraglottic airway comprising:

a supraglottic bowl defining a distal end, a neck extending outward of the supraglottic bowl and defining a proximal end, a longitudinally extending intubation conduit formed therethrough, the supraglottic bowl including a cuff and defining a bowl surface, wherein the intubation conduit extends from the proximal end of the neck to an opening in the bowl surface, and wherein the intubation conduit is configured to have an endotracheal tube (ETT) inserted therethrough;

an intubation conduit occluding feature;

a reduced diameter portion within the intubation conduit, wherein the reduced diameter portion has a diameter slightly smaller than an outside diameter of one of the ETT that will be inserted therethrough and an introducing stylet upon which the ETT may be mounted, and defines an expandable aperture within the intubation conduit, and wherein the expandable aperture is configured to stretch open as an inside wall of the expandable aperture engages and maintains an airtight seal around the one of the ETT and the introducing stylet during ventilation of air via the fluid flow channels; and at least one fluid flow channel formed longitudinally through a wall of the supraglottic airway, collaterally to the intubation conduit and from the proximal end to the bowl surface within the supraglottic bowl.

28. The bi-functional intubating and ventilating supraglottic airway according to claim 27, wherein the at least one fluid flow channel is configured as a ventilation channel for the flow of air from the proximal end to the supraglottic bowl.

29. The bi-functional intubating and ventilating supraglottic airway according to claim 28, wherein the supraglottic airway further includes a fluid flow tube connected within the ventilation channel, and a 15 mm connector at a proximal end of the fluid flow tube.

30. The bi-functional intubating and ventilating supraglottic airway according to claim 29, further including a connector configured to releasably connect the fluid flow tube to one of the ETT and an introducing stylet upon which the ETT is positioned.

31. A bi-functional intubating and ventilating supraglottic airway comprising:

a supraglottic bowl defining a distal end, a neck extending outward of the supraglottic bowl and defining a proximal end, a longitudinally extending intubation conduit formed therethrough, the supraglottic bowl including a cuff and defining a bowl surface, wherein the intubation conduit extends from the proximal end of the neck to an opening in the bowl surface, and wherein the intubation conduit is configured to have an endotracheal tube (ETT) inserted therethrough;

at least one fluid flow channel formed longitudinally through a wall of the supraglottic airway, collaterally to the intubation conduit and from the proximal end to the bowl surface within the supraglottic bowl; and a split-capable feature extending along an entire length of the intubation conduit, the split-capable feature extending through the neck, the cuff, and the bowl surface, wherein the split capable feature includes one or more cuts along a line that defines a location for a slot, the cuts penetrating through only a portion of a thickness of a wall of the supraglottic airway, such that the split capable feature is airtight and un-opened until urged open by a user to define the slot.

\* \* \* \* \*